United States Patent [19]
Schilling et al.

[11] B 3,985,774

[45] Oct. 12, 1976

[54] PURIFICATION OF γ-OXO-2-DIBENZOFURANBUTYRIC ACID

[75] Inventors: Guenther Schilling, Westmount; Thomas A. Dobson, Dollard-Des-Ormeaux, both of Canada

[73] Assignee: American Home Products Corporation, New York, N.Y.

[22] Filed: Oct. 30, 1972

[21] Appl. No.: 302,160

[44] Published under the second Trial Voluntary Protest Program on February 3, 1976 as document No. B 302,160.

[52] U.S. Cl. .................... 260/346.2 M; 424/285
[51] Int. Cl.² .............................. C07D 307/80
[58] Field of Search ........ 260/346.2 R, 525, 475 B

[56] References Cited
UNITED STATES PATENTS

| | | | |
|---|---|---|---|
| 2,513,273 | 7/1950 | Burtner et al. | 260/515 |
| 2,569,440 | 10/1951 | Agnew et al. | 260/525 |
| 2,733,266 | 1/1956 | McKinnis | 260/525 |
| 2,773,091 | 12/1956 | Burtner | 260/515 |
| 2,813,120 | 11/1957 | McKinnis | 260/525 |
| 3,649,651 | 3/1972 | Dobson | 260/346.2 |

OTHER PUBLICATIONS

Keumi et al., Kogyo Kagaku Zasshi, vol. 73, pp. 536–538, (1970).

Keumi et al., Kogyo Kagaku Zasshi, vol. 73, pp. 2412–2421, (1970).

Patai, The Chemistry of Carboxylic Acids and Esters, pp. 897–905, (1969).

Gunther et al., J. Pharmacol, Exptl. Therap 99, No. 4, Pt. 1, pp. 465–478, 1950.

Chatterjea, J. N., Jour. Indian Chem. Soc., vol. 33, No. 7, 1956, p. 453.

*Primary Examiner*—Harry I. Moatz

[57] ABSTRACT

A process for the separation of γ-oxo-2-dibenzofuranbutyric acid from a mixture of said acid and γ-oxo-3-dibenzofuranbutyric acid is disclosed. Such a mixture is obtained by the prior art method of preparing γ-oxo-2-dibenzofuranbutyric acid from dibenzofuran and succinic anhydride in a Friedel-Crafts reaction. The mixture of acids is converted to a mixture of their corresponding lower alkyl esters which is separated by recrystallization or chromatography into its component alkyl esters. Hydrolysis of the lower alkyl ester of γ-oxo-2-dibenzofuranbutyric acid gives the desired corresponding acid.

2 Claims, No Drawings

PURIFICATION OF γ-OXO-2-DIBENZOFURANBUTYRIC ACID

BACKGROUND OF THE INVENTION a. Field of the Invention

This invention relates to a process for the purification of γ-oxo-2-dibenzofuranbutyric acid. The latter compound and its water soluble pharmaceutically acceptable salts are useful as antiinflammatory agents.

b. Prior Art

The compound γ-oxo-2-dibenzofuranbutyric acid has been described by F. Mayer and W. Krieger, Chem. Ber., 55B, 1659 (1922) and by H. Gilman, et al., J. Amer. Chem. Soc., 61, 2842 (1939). The compound is represented by formula I:

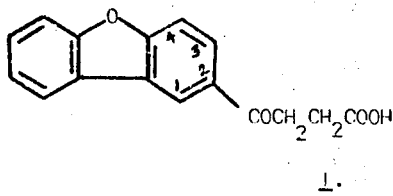

The co-pending Application of T. A. Dobson and J. G. Rochefort, Ser. No. 50,296, filed June 26, 1970, now U.S. Pat. No. 3,728,349, issued Apr. 17, 1973, described in detail the results of pharmacologic testing of γ-oxo-2-dibenzofuranbutyric acid as prepared by the procedures of Gilman et al., cited above, and such results are incorporated herein by reference. Application Ser. No. 50,296 also describes and claims dosage forms for the method of treatment of inflammatory conditions employing γ-oxo-2-benzofuranbutyric acid and the description of such dosage forms is also incorporated herein by reference.

It has now been found that the above compound possesses important antiinflammatory properties and a low order of toxicity, which makes it particularly valuable for use as an antiinflammatory agent in the treatment of inflammatory conditions. The compound is also exceptionally well tolerated upon prolonged administration of high doses and possesses a highly favorable therapeutic index. The compound also possesses analgesic and antipyretic activity.

As an added advantage, the compound does not cause formation of gastrointestinal ulcers when tested at therapeutic dose levels for ulcerogenic activity in a modification of a known method.

The compound, γ-oxo-2-dibenzofuranbutyric acid, which has only limited solubility in water, is easily transformed into a highly water-soluble pharmaceutically acceptable salt thereof by titrating with a water-soluble base; for example, an alkali metal, alkaline earth metal, ammonium or substituted ammonium hydroxide, or with an organic base. The preferred salt is the sodium salt, obtainable from the free acid by titrating with sodium hydroxide.

These salts of γ-oxo-2-benzofuranbutyric acid exhibit the same pharmacological activity as the parent acid when administered to animals.

A preparation of the useful agent of this invention, γ-oxo-2-dibenzofuranbutyric acid, is described by H. gilman, et al., cited above. On first glance, this reported preparation appears to be both convenient and practical. According to this report, the useful agent of this invention is obtained directly by the reaction of dibenzofuran and succinic anhydride in a Friedel-Crafts type reaction. Furthermore, Gilman states that this method gives an 83% yield of the purified γ-oxo-2-dibenzofuranbutyric acid.

However, in contradistinction to the report, a close examination of this product with today's methods for detecting homogeneity, for example, gas liquid chromatography (glc), shows that the product of the Gilman procedure is not purified γ-oxo-2-dibenzofuranbutyric acid (I) but rather a mixture. This mixture consists of the desired acid II and a significant amount of its isomer, γ-oxo-3-dibenzofuranbutyric acid (II).

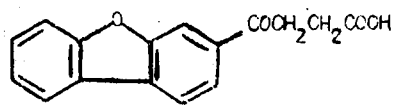

Although both the desired acid I and the isomer II have antiinflammatory activity, and although both may be used for this purpose in the manner described herein for the acid I, the said acid I has been found to be somewhat more active and have a quicker onset of action. Accordingly, a process for separating these two acids has become of significant importance.

The presence of this isomer in the product of this preparation presents a difficult problem with regard to its separation from the desired acid I. The difficulty is mainly due to the isomer II possessing many similar physical characteristics of the desired acid I. Thus, the direct separation of the isomer II from the desired acid I on a reasonable scale by conventional means has proven to be an unfeasible and impractical operation to date. For example, crystallization of the mixture of acids from various solvents, for example, toluene, ethyl acetate and methanol, does not change substantially the relative proportions of the two acids in the mixture.

Accordingly, it is the purpose of this invention to disclose a method whereby the isomer II can readily be removed from the above mixture so that the desired acid I is obtained in a pure form.

For many reasons, including the sophisticated and exacting requirements of manufacturing and government organizations to control and maintain the quality of a drug, it is desirable to be able to prepare the drug in its highest possible state of purity.

SUMMARY OF THE INVENTION

The process of this invention involves a method for separating a first acid, γ-oxo-2-dibenzofuranbutyric acid from a mixture of the first acid, present in an amount of at least 80% by weight of the mixture, and its isomeric, second acid, γ-oxo-3-dibenzofuranbutyric acid. The method comprises:

1. subjecting the mixture of the first and second acids to esterification conditions to obtain a mixture of the corresponding lower alkyl esters,
2. separating the mixture of the esters into the lower alkyl ester of γ-oxo-2-dibenzofuranbutyric acid and the lower alkyl ester of γ-oxo-3-dibenzobutyric acid, and
3. subjecting the lower alkyl ester of γ-oxo-2-dibenzofuranbutyric acid to hydrolysis conditions to obtain its corresponding acid, the said first acid.

DETAILS OF THE INVENTION

The term "lower alkyl" as used herein contemplates straight chain alkyl radicals containing from one to six carbon atoms and branched chain alkyl radical containing up to four carbon atoms and includes methyl, ethyl, propyl, isopropyl, butyl, isobutyl, pentyl, hexyl, and the like.

The term "lower alkanol" as used herein contemplates straight chain aliphatic alcohols containing from one to six carbon atoms and branched chain aliphatic alcohols containing from one to four carbon atoms and includes methanol, ethanol, isopropanol, t-butanol, pentanol, hexanol, and the like.

The useful antiinflammatory, analgesic and antipyretic activities of the product of this invention is demonstrable in standard pharmacologic tests, for example, the test described by R. A. Turner in "Screening Method in Pharmacology", Academic Press, New York and London, 1965, pp. 152–163, pp. 100–117 and pp. 298–299, respectively.

The lack of side effects for the compound of formula I may be demonstrated by standard acute toxicity tests (see Turner cited above) and by prolonged administration of the compound to warm-blooded animals.

More particularly, the antiinflammatory activity of the compound of formula I, as well as the isomer II, is readily demonstrated in the carragheenin paw edema test described by C. A. Winter, et al., Proc. Soc. Exp. Biol., III, 544 (1962). According to Winter this test correlates well with data derived from clinical results with humans, and has demonstrated such a correlation with indomethacin, hydrocortisone, mefenamic acid and flufenamic acid, see C. A. Winter in "Non-Steroidal Anti-inflammatory Drugs", S. Garattine and M. N. G. Dukes, Eds., Excerpta Medica International Congress, Ser. No. 82, 1965, p. 190.

More particularly exemplified a substantial effect for γ-oxo-2-dibenzofuranbutyric acid is demonstrable at oral doses of 200 mg/kg or less in this paw edema test. In this test rats are treated with the test compound one hour before a 1% suspension of carragheenin in saline is injected into the subplantar area of the hind paw of the rat. Results are obtained by measuring the increase in paw volume caused by the resulting edema three hours later by plethysmography in mercury and expressing values as grams of mercury displaced. Control animals receive the vehicle only. The results are expressed as percent inhibition in edematous swelling calculated as $$\frac{\Delta_{control} - \Delta_{treated} \times 100}{\Delta_{control}},$$

where $\Delta$ control is the increase in volume measured in untreated controls and $\Delta$ treated is the increase in volume found in the treated animals.

The following table lists the results obtained for both γ-oxo-2-dibenzofuranbutyric acid (I) and its isomer II. The standard errors of all values are calculated and shown in the table below. The results are evaluated statistically and according to Student's t test the acid I is significantly more active than the isomer II.

TABLE

| COMPOUND | EFFECT ON CARRAGHEENIN PAW EDEMA | | |
|---|---|---|---|
| | DOSE MG/KG | EDEMA * | %INHIBITION |
| Experiment A | | | |
| None | — | 12.3 ± 0.65 | — |
| γ-oxo-2-benzofuran-butyric acid | 200 | 2.7 ± 0.36 | 78 |
| | 100 | 5.7 ± 0.42 | 54 |
| | 50 | 7.7 ± 0.88 | 37 |
| Experiment B | | | |
| None | — | 14.3 ± 2.2 | — |
| γ-oxo-3-benzofuran-butyric acid | 400 | 10.3 ± 1.05 | 28 |
| | 200 | 9.5 ± 1.11 | 34 |
| | 100 | 13.6 ± 1.38 | 5 |
| Experiment C | | | |
| None | — | 12.1 ± 0.43 | — |
| γ-oxo-2-benzofuran-butyric acid | 100 | 4.8 ± 0.46 | 60 |
| γ-oxo-3-benzofuran-butyric acid | 100 | 9.9 ± 0.67 | 18 |

* Results are expressed in grams of mercury displaced. In this test γ-oxo-3-benzofuranbutyric acid is significantly $P<0.01$ (+ test) less active than γ-oxo-2-benzofuranbutyric acid (Experiment C).

When γ-oxo-2-dibenzofuranbutyric acid is employed as an antiinflammatory, antipyretic or analgesic agent in warm-blooded animals, e.g., rats, it may be administered orally, alone or in dosage forms, i.e., capsules or tablets, combined with pharmacologically acceptable excipients, such as starch, milk sugar and so forth. The compound may also be administered orally in the form of solutions in suitable vehicles such as vegetables oils.

The dosage of the active agent of this invention will vary with the particular compound chosen and form of administration. Furthermore, it will vary with the particular host under treatment. Generally, the active agent of this invention is administered at a concentration level that affords protective effects without any deleterious side effects. These antiinflammatorily-antipyretically-analgesically effective concentration levels are usually obtained within a therapeutic range of 1.0 mg to 500 mg/kg per day, with a preferred range of 10 to 100 mg/kg per day.

In practising the process of this invention, the product obtained by the reaction of dibenzofuran and succinic anhydride, described above, is used as starting material. This product is actually a mixture of the desired acid, γ-oxo-2-dibenzofuranbutyric acid (I) and its structural isomer, γ-oxo-3-dibenzofuranbutyric acid (II). Examination of this product by glc indicates that it is about a 9 to 1 mixture of the desired acid I and the isomer II.

This mixture of acids is subjected first to esterification conditions whereby the mixture is converted to a corresponding mixture of lower alkyl esters.

Suitable esterification conditions include a variety of methods; for example, ester exchange, treatment with diazomethane, or conversion of the mixture of acids to a mixture of corresponding acid halides or mixed anhydrides followed by treatment of the latter with an appropriate lower alkanol, see also L. F. Fieser and M. Fieser, "Advanced Organic Chemistry", Reinhold Publishing Corporation, New York. 1961, pp. 370–381.

Preferred esterification conditions involve the treatment of the mixture of acids with a lower alkanol, for example, methanol, ethanol, n-propanol or the like, in the presence of a suitable acid catalyst, for example, hydrochloric acid, sulfuric acid, perchloric acid, boron trifluoride etherate and the like.

The choice of temperature and duration of the reaction time for performing the esterification is not critical but is largely dependent on the catalyst and lower alkanol used for the reaction. Usually it is most convenienet to carry out the reaction at temperatures ranging from 20°C to the boiling point of the mixture for a period of 15 minutes to 24 hours.

In a preferred embodiment the esterification is performed by dissolving the mixture of the acid in 10 to 25 parts (w/v) of methanol. Concentrated hydrochloric acid (1/10 to ⅛ volume per weight of the mixture of acids) is then added and the resulting mixture is heated to reflux and boiled for 30 minutes. The mixture of esters is isolated by diluting the cooled reaction mixture with water and separating the resulting solid.

The mixture of esters is then fractionally cyrstallized from a suitable solvent. Suitable solvents for the crystallization include aromatic hydrocarbons, for example, toluene, benzene or o-xylene; lower alkyl lower alkanoates, for example, ethyl acetate, methyl propionate or butyl acetate; lower halogenated hydrocarbons, for example, chloroform, carbon tetrachloride, ethylene dichloride; as well as other non-reactive solvents, for instance, the lower alkanols, for example, methanol or ethanol, lower aliphatic ketones, for example, acetone or methyl ethyl ketone, dimethyl sulfoxide, N,N-dimethylformamid and acetonitrile. Toluene and methanol are especially convenient and quite suitable solvents for this purpose.

Preferably, a 5 to 10% (w/v) solution of the mixture of esters, obtained as described above, is prepared in one of the aforementioned solvents. Generally, the appropriate amounts of the mixture of esters and solvents are warmed together until solution is achieved. Thereafter, cooling of the solution results in preferentiial crystallization of the desired acid I.

During the preceding operation the temperature range covering the heating and cooling is chosen by practical considerations, i.e., the boiling point of the solvent, solubility of the mixture, bath temperature of the cooling bath, etc. For example, in the case where toluene is used as the solvent, the mixture of the esters and toluene (5 to 10%, w/v) can be heated from 40°C to the boiling point of toluene (111°C) and then cooled to below 40°C, the temperature difference being sufficient to provide a high yield of crystals. Thereafter, the crystallizing mixture is maintained at the lower temperature until crystallization is complete, usually for longer than 15 minutes and preferable over one hour. The crystals are separated from the resultant mixture, for example, by filtration. In this manner the purified lower alkyl ester of γ-oxo-2-dibenzofuranbutyric acid (>99% pure) is isolated.

Alternatively the mixture of the lower alkyl esters may be separated by chromatography. Several types of absorbents may be used for this purpose. Silica gel and neutral alumina are preferred absorbents although other types of alumina may also be used. Moreover, a variety of solvent systems may be used as the eluant, for example, methylenedichloride-ether, hexane-methanol or benzenechloroform. The latter system is particularly convenient and efficacious with silica gel. In the latter case the mixture of esters is put on the column with benzene or benzene-chloroform (10:1). By decereasing the ratio of benzene-chloroform stepwise to (1:1) the lower alkyl ester of the desired acid I is eluted first from the column, followed by elution of mixtures of the desired acid I and the isomer II and finally the pure isomer II. Subsequent concentration of the eluant containing the lower alkyl ester of the desired acid I affords the ready isolation of the ester. Likewise, the isomer II is also obtained.

The lower alkyl ester of the desired acid I is converted to the desired acid I (>99% pure) by treatment with a hydrolyzing agent under hydrolysis conditions. Generally speaking, this conversion is most conveniently performed by employing a base as the hydrolyzing agent. The hydrolysis is performed in the presence of sufficient water, followed by acidification of the reaction mixture to yield the desired acid. However, it should be understood that the manner of hydrolysis for the process of this invention is not intended to be limited to basic hydrolysis since hydrolysis under acidic conditions and other variations, for example, treatment with lithium iodide in collidine (see L. F. Fieser and M. Fieser, "Reagents for Organic Synthesis", John Wiley and Sons, Inc., New York, 1967, pp. 615–617), are also applicable.

For basic hydrolysis a preferred embodiment involves subjecting the lower alkyl ester to the action of a strong base, for example, sodium or potassium hydroxide, in the presence of sufficient water to effect hydrolysis of the ester. The hydrolysis is performed using a suitable solvent, for example, methanol or ethanol.

The reaction mixture is maintained at a temperature of from 25°C. to the reflux temperature until hydrolysis occurs. Usually from 10 minutes to 6 hours is sufficient for this hydrolysis. The reaction mixture is then rendered acidic with an acid, for example, acetic acid, hydrochloric acid, sulfuric acid and the like, to release the free acid as a solid.

Alternatively, the reaction mixture is mixed with a solution of a hydrolyzing agent which is a strong organic or inorganic acid, for example, trifluoroacetic acid, p-toluenesulfonic acid, hydrochloric acid, hydrobromic acid, hydroiodic acid, sulfuric acid, phosphoric acid and the like at a temperature of at least 60°C. and preferably from 90°C. to the boiling point of the mixture until the hydrolysis occurs. Usually from 5 to 24 hours are required for this hydrolysis. Suitable solvents for the acid include water, acetic acid, aqueous alcohols and the like. If acid hydrolysis is used, the free acid is formed directly. If necessary, the reaction mixture can be diluted with water to precipitate the product.

Similarly, and if desired, the isomer II is obtained by hydrolysis of the lower alkyl ester of the isomer II obtained as described above.

EXAMPLE 1

γ-Oxo-2-dibenzofuranbutyric acid (I) and γ-Oxo-3-dibenzofuranbutyric acid (II)

A mixture of the title compounds is prepared according to the procedure of Gilman, et al., cited above.

An exemplification of this procedure is as follows:

A stirred mixture of 50 kg. of dibenzofuran in 200 liters of methylene chloride is treated with 20 kg. of succinic anhydride. The resulting suspension is cooled to 5°C. and to this is added, over a period of 3 hr., 54 kg. of anhydrous aluminum chloride, keeping the temperature between 5° to 8°C. The mixture is stirred at 24°C. for 20 hr.

This mixture is then quenched in a cold mixture of 300 liters of 30% hydrochloric acid and 300 liters of ice water slurry. The resulting precipitate is collected and washed with water.

The wet solid precipitate is dissolved in 200 liters water containing 24 kg. of 45% aqueous potassium hydroxide solution and the solution is washed with ethyl acetate (1 × 60 liters + 1× 40 liters). To the aqueous alkaline phase is added 4 kg. of charcoal and the mixture is stirred for 1 hr. at room temperature. The charcoal is removed by filtration through a diatomaceous earth (Celite) pad. The filter cake is washed with water.

The filtrate and washing is adjusted to pH 4.5 with glacial acetic acid (required 42 liters) and the precipitate is collected and washed with water. The damp solid (m.p. 182° – 184°C) is dissolved in 700 liters of isopropanol by warming to 80°C. and the hot solution is clarified by filtering through a diatomaceous earth pad. The filter cake is washed with 50 liters of hot isopropanol and the filtrate and wash are combined, concentrated under reduced pressure to 240 liters and the concentrate is cooled to 10°C. and stirred at this temperature overnight with slow agitation. The crystals which separate are collected by filtration, washed with isopropanol and dried in a vacuum oven at 60°C. for 40 hours to yield a mixture of the title compounds in about at 9:1 ratio (w/w), respectively.

The ratio of the two title compounds in the product mixture is determined by glc of their corresponding methyl esters (see Example 2). For instance, by using a 12 ft., 2.8 mm ID column (15% Se-30 on GCO 80 – 100 mesh, i.e. 15% dimethylpolysiloxane on calcinated, acid and solvent washed and then silanized diatomaceous earth, obtained from Applied Science Laboratories, State College, Penn.) at 255°C. and a flow of 30 ml/min, the isomeric esters are separated.

EXAMPLE 2

γ-Oxo-2-dibenzofuranbutyric acid methyl ester

A mixture of 43.2 kg. of the mixture of the acids as prepared in Example 1, 1050 liters of methanol and 5.4 liters of hydrochloric acid is warmed to reflux over a period of 25 minutes and then boiled for 1 hr. [Examination of the reaction mixture by tlc ($SiO_2$, benzene) using sulfuric acid as a spray indicates the esterification is complete after 30 minutes of boiling.] The resultant solution is cooled. The precipitated crystals are collected. The crystals (dry weight = about 42.5 kg.) are not dried but are dissolved in 400 liters of toluene by warming to 90°C. The solution is then cooled with slow stirring to 28°C. over 6 hr. The crystals are collected. On glc examination, see Example 1, this product is shown to be almost free of the isomer II methyl ester (<1%). Without drying, these crystals are dissolved in 55 liters of toluene by warming to 90°C., and the solution cooled to 0°C. with slot agitation. The crystals are collected by filtration, washed with 10 liters of toluene and dried at 65°C. under reduced pressure to give the title compound as purified, colorless crystals, m.p. 118.5° – 119°C.

In the same manner but replacing methanol with an equivalent amount of ethanol, or n-propanol, γ-oxo-2-dibenzofuranbutyric acid ethyl and propyl ester are obtained, respectively.

In the same manner but replacing the toluene with benzene, ethyl acetate or methanol the title compound is also obtained.

EXAMPLE 3

Purified γ-Oxo-2-dibenzofuranbutyric acid

A mixture of 51.4 kg. of γ-oxo-2-dibenzofuranbutyric acid methyl ester, m.p. 118.5° – 119°C., prepared as described in Examples 2 or 4, 210 liters of water, 52 liters of methanol and a solution of 10.6 kg. of sodium hydroxide flakes dissolved in 10 liters of water is stirred at 75° – 77°C. for 75 minutes, cooled to 40°C. and the pH adjusted to 2.2 with hydrochloric acid. The white crystalline suspension is cooled to 30°C. and the precipitate is collected by filtration, washed by stirring with 300 liters of water, and then collected by filtration, washed on the filter with water and dried in a vacuum oven at 75°C. for 48 hr.

A mixture of the dried acid obtained above (56.7 kg.) and 1500 liters of acetone is refluxed for 1 hr. The cloudy solution is filtered through paper to clarify it and the pale straw coloured filtrate is concentrated to a volume of 280 liters. The residue is cooled to −5°C. and the crystals are collected by filtration, washed on the filter with 40 liters of cold acetone (−5°C.) and dried in the vacuum oven at 45°C. for 12 hours to yield the purified γ-oxo-2-dibenzofuranbutyric acid, m.p. 189° – 190°C. (greater than 99% pure).

In the same manner but replacing γ-oxo-2-dibenzofuranbutyric acid methyl ester with an equivalent amount of γ-oxo-3-dibenzofuranbutyric acid methyl ester, described in Example 4, there is obtained γ-oxo-3-dibenzofuranbutyric acid, m.p. 208° – 210°C., after recrystallization from ethanol.

In the same manner but replacing γ-oxo-2-dibenzofuranbutyric acid methyl ester with its corresponding ethyl or propyl ester, described in Example 2, the title compound is also obtained.

EXAMPLE 4

A modification of the procedure of Example 2 is effected whereby the precipitated crystals from the reaction mixture are dried.

Thereafter the dried crystals, a mixture of the methyl esters of both acids I and II, (10.00 g.) are dissolved in 300 ml. of benzene and poured onto a column of 500 g. of silica gel. After washing the column with benzene, further elution with 800 ml. fractions of benzene-chloroform (10:1), followed by elution with benzene-chloroform (1:1) affords the purified γ-oxo-2-dibenzofuranbutyric acid methyl ester, described in Example 2, followed by later fractions containing a mixture of the methyl esters of the acids of formulae I and II and finally fractions of pure γ-oxo-3-dibenzofuranbutyric acid methyl ester, m.p. 106° – 108°C. after recrystallization from benzene.

The same results are also obtained by replacing silica gel with neutral alumina.

EXAMPLE 5

γ-Oxo-2-dibenzofuranbutyric acid (25 g), prepared as described in Example 3, is mixed with 175 g lactose, 44 g starch, 4 g magnesium stearate, and 2 g sucrose. The mixture is granulated with addition of a small amount of ethyl alcohol, dried, milled, and compressed into tablets weighing 250 mg each or filled into capsules in amounts of 250 mg each, to make 1000 tablets or capsules containing 25 mg of the active ingredient per tablet or capsule.

In the same manner, but using 50 g γ-oxo-2-dibenzofuranbutyric acid, prepared as described in Example 3, and 150 g lactose, together with the same amounts of starch, magnesium stearate, and sucrose as above, 1000 tablets or capsules containing 50 mg of the active ingredient per tablet or capsule are obtained.

EXAMPLE 6

γ-Oxo-2-dibenzofuranbutyric acid (25 g), prepared as described in Example 3, is dissolved in pyrogen-free water (900 ml) by adjusting the pH to 7.5-8.5 with sodium hydroxide solution and adding sufficient sodium chloride or sodium citrate or glucose to make the solution isotonic. A preservative such as 0.1 percent weight by volume of methylparaban and 0.015 percent weight by volume of propylparaban or 0.5 percent weight by volume of chlorbutanol is added, the solution is made up to 1000 ml. sterilized by filtration of autoclaving, and filled into sterile ampoules or vials, to make a solution for parenteral administration containg 25 mg of the active ingredient per milliliter.

In the same manner, but using 50 g of γ-oxo-2-dibenzofuranbutyric acid, prepared as described in Example 3, and proceeding as above but without addition of sodium chloride or citrate or glucose, a solution containing 50 mg/ml of the active ingredient is obtained.

Again in the same manner, but using, instead of sodium hydroxide, lithium, potassium, calcium, or ammonium hydroxide, or aqueous solutions of methylamine, dimethylamine, trimethylamine, ethylamine, diethylamine, triethylamine, methyl-ethylamine, mono-, di-, or triethanolamine, ethylenediamine, hexamethylenediamine, pyrrolidine, piperidine, morpholine, piperazine, N-methylmorpholine, N-(2-hydroxyethyl)piperidine, or pyridine, or quaternary bases containing the tetramethyl, methyl-triethanol, or trimethyl-monoethanol ammonium ion, or the N-methylpyridinium, N-methyl-N-(2-hydroxyethyl)-pyrrolidinium, N,N-dimethylmorpholinium, N-methyl-N-(2-hydroxyethyl)-morpholinium, N,N-dimethyl-piperidinium ions, the corresponding salts of γ-oxo-2-dibenzofuranbutyric acid are also obtained.

EXAMPLE 7

γ-Oxo-2-dibenzofuranbutyric acid (50 g), prepared as described in Example 3, is sterilized by autoclaving. The sterile solid is mixed under sterile conditions with 970 ml of sterile sesame oil and 15 ml of sterile benzyl alcohol, and make up to 1000 ml with sterile sesame oil, to make a sterile suspension for parenteral administration containing 50 mg/ml of the active ingredient, which is filled into sterile vials under sterile conditions.

In the same manner, but using an aqueous suspension of carboxymethylcellulose instead of sesame oil and dispersing the γ-oxo-2-dibenzofuranbutyric acid with a mechanical blender and sterilizing by autoclaving, a sterile aqueous suspension containing 50 mg/ml of the active ingredient is obtained and filled into sterile ampoules or vials.

I claim:

1. A process for separating γ-oxo-2-dibenzofuranbutyric acid from a mixture of said acid with γ-oxo-3-dibenzofuranbutyric acid, the γ-oxo-2-dibenzofuranbutyric acid constituting at least 80% by weight of the said mixture, which comprises
   1. admixing the acid mixture with a solvent comprising methanol or ethanol;
   2. esterifying the solution of the acid mixture in the presence of an acid esterification catalyst;
   3. separating the ester mixture from the solution by the addition of water and/or cooling to precipitate the resulting ester mixture;
   4. dissolving the ester mixture in toluene;
   5. fractionally precipitating the γ-oxo-2-dibenzofuranbutyric acid ester from the toluene solution; and
   6. hydrolyzing with a base the ester to provide essentially pure γ-oxo-2-dibenzofuranbutyric acid.

2. A process for separating γ-oxo-2-dibenzofuranbutyric acid from a mixture of said acid with γ-oxo-3-dibenzofuranbutyric acid, the γ-oxo-2-dibenzofuranbutyric acid constituting at least 80% by weight of the said mixture, which comprises
   1. admixing the acid mixture with a solvent comprising methanol or ethanol;
   2. esterifying the solution of the acid mixture in the presence of an acid esterification catalyst;
   3. separating the ester mixture from the solution by the addition of water and/or cooling to precipitate the resulting ester mixture;
   4. separating the γ-oxo-2-dibenzofuranbutyric acid ester from the mixture of esters by column chromotography on silica gel or neutral alumina followed by selective elution; and
   5. hydrolyzing with a base the ester to provide essentially pure γ-oxo-2-dibenzofuranbutyric acid.

* * * * *